(12) United States Patent
Smith

(10) Patent No.: US 8,979,883 B2
(45) Date of Patent: Mar. 17, 2015

(54) OBTURATOR TIP

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 399 days.

(21) Appl. No.: 12/943,311

(22) Filed: Nov. 10, 2010

(65) Prior Publication Data
US 2011/0152753 A1    Jun. 23, 2011

Related U.S. Application Data

(60) Provisional application No. 61/287,411, filed on Dec. 17, 2009.

(51) Int. Cl.
*A61M 29/00* (2006.01)
*A61B 17/34* (2006.01)

(52) U.S. Cl.
CPC ......... *A61B 17/3496* (2013.01); *A61B 17/3421* (2013.01)
USPC ....... 606/191; 604/164.01; 606/184; 606/185

(58) Field of Classification Search
CPC ............... A61B 17/3417; A61B 17/34; A61B 17/3401; A61B 17/3403
USPC ......... 606/190, 191, 167, 184, 185, 170, 171; 604/104, 164.01–164.13, 264, 506; 407/57, 63; 30/164.8, 164.5, 167, 30/167.1
See application file for complete search history.

(56) References Cited

U.S. PATENT DOCUMENTS

| | | |
|---|---|---|
| 1,882,213 A | 10/1932 | Donovan |
| 2,566,738 A | 9/1951 | Mitchell |
| 3,652,100 A | 3/1972 | Baturka |
| 3,760,810 A | 9/1973 | Hoorn |
| 4,535,773 A | 8/1985 | Yoon |
| 4,601,710 A | 7/1986 | Moll |
| 4,607,619 A | 8/1986 | Seike et al. |

(Continued)

FOREIGN PATENT DOCUMENTS

| | | |
|---|---|---|
| EP | 0 426 407 B1 | 5/1991 |
| EP | E 0 604 197 | 6/1994 |

(Continued)

OTHER PUBLICATIONS

European Search Report for corresponding EP06001607 dated Mar. 13, 2006.

(Continued)

*Primary Examiner* — Katrina Stransky

(57) ABSTRACT

A surgical instrument for use with a surgical portal apparatus includes an elongate shaft defining a longitudinal axis. A dilating member disposed at a distal end of the elongate shaft and has a first longitudinal arc segment and a second longitudinal arc segment being in diametrical opposed relation. The first and second longitudinal arc segments define respective first and second radii of curvature transverse to the longitudinal axis, and decrease from proximal to distal to define a generally tapered configuration of the dilating member. The first radius of curvature is greater than the second radius of curvature at predefined longitudinal positions of the dilating member such that the first longitudinal arc segment extends distally beyond the second longitudinal segment to define a penetrating tip. The penetrating tip has a reduced profile and is dimensioned to facilitate initial insertion of the dilating member into tissue.

23 Claims, 2 Drawing Sheets

(56) References Cited

U.S. PATENT DOCUMENTS

| | | |
|---|---|---|
| 4,654,030 A | 3/1987 | Moll et al. |
| 4,700,694 A | 10/1987 | Shisido |
| 4,705,023 A | 11/1987 | Arai |
| 4,802,487 A | 2/1989 | Martin et al. |
| 4,878,485 A | 11/1989 | Adair |
| 5,066,288 A | 11/1991 | Deniega et al. |
| 5,104,382 A | 4/1992 | Brinkerhoff et al. |
| 5,169,397 A | 12/1992 | Sakashita et al. |
| 5,215,526 A | 6/1993 | Deniega et al. |
| 5,217,441 A | 6/1993 | Shichman |
| 5,224,951 A | 7/1993 | Freitas |
| 5,224,952 A | 7/1993 | Deniega et al. |
| 5,226,890 A | 7/1993 | Ianniruberto et al. |
| 5,226,891 A | 7/1993 | Bushatz et al. |
| 5,232,440 A | 8/1993 | Wilk |
| 5,248,298 A | 9/1993 | Bedi et al. |
| 5,250,068 A | 10/1993 | Ideguchi et al. |
| 5,256,149 A | 10/1993 | Banik et al. |
| 5,263,937 A | 11/1993 | Shipp |
| 5,271,380 A | 12/1993 | Rlek et al. |
| 5,279,597 A | 1/1994 | Dassa et al. |
| 5,290,276 A | 3/1994 | Sewell |
| 5,308,336 A | 5/1994 | Hart |
| 5,314,417 A | 5/1994 | Stephens et al. |
| 5,334,150 A | 8/1994 | Kaali |
| 5,336,206 A | 8/1994 | Shichman |
| 5,354,302 A | 10/1994 | Ko |
| 5,364,372 A | 11/1994 | Danks et al. |
| 5,366,445 A | 11/1994 | Haber et al. |
| 5,370,640 A | 12/1994 | Kolff |
| 5,372,588 A | 12/1994 | Farley et al. |
| 5,376,076 A | 12/1994 | Kaali |
| 5,380,291 A | 1/1995 | Kaali |
| 5,380,302 A | 1/1995 | Orth |
| 5,385,553 A | 1/1995 | Hart |
| 5,385,572 A | 1/1995 | Nobles et al. |
| 5,387,197 A | 2/1995 | Smith et al. |
| 5,391,152 A | 2/1995 | Patterson |
| 5,399,167 A | 3/1995 | Deniega |
| 5,408,992 A | 4/1995 | Hamlin et al. |
| 5,411,515 A | 5/1995 | Haber et al. |
| 5,431,151 A | 7/1995 | Riek et al. |
| 5,441,041 A | 8/1995 | Sauer et al. |
| 5,445,142 A | 8/1995 | Hassler |
| 5,467,762 A | 11/1995 | Sauer et al. |
| 5,471,705 A | 12/1995 | Dao |
| 5,478,317 A | 12/1995 | Yoon |
| 5,487,745 A | 1/1996 | McKenzie |
| 5,496,259 A | 3/1996 | Perkins |
| 5,522,833 A | 6/1996 | Stephens et al. |
| 5,533,977 A | 7/1996 | Metcalf et al. |
| 5,534,009 A | 7/1996 | Lander |
| 5,538,509 A | 7/1996 | Dunlap et al. |
| 5,545,150 A | 8/1996 | Danks et al. |
| 5,551,947 A | 9/1996 | Kaali |
| 5,554,137 A | 9/1996 | Young et al. |
| 5,554,167 A | 9/1996 | Young et al. |
| 5,562,696 A | 10/1996 | Nobles et al. |
| 5,569,160 A | 10/1996 | Sauer et al. |
| 5,569,291 A | 10/1996 | Privitera et al. |
| 5,569,292 A | 10/1996 | Scwemberger et al. |
| 5,571,133 A | 11/1996 | Yoon |
| 5,591,191 A | 1/1997 | Kieturakis |
| 5,591,192 A | 1/1997 | Privitera et al. |
| 5,601,559 A | 2/1997 | Melker et al. |
| 5,607,440 A | 3/1997 | Danks et al. |
| 5,609,562 A | 3/1997 | Kaali |
| 5,609,604 A | 3/1997 | Schwemberger et al. |
| 5,620,188 A | 4/1997 | McCurry et al. |
| 5,624,459 A | 4/1997 | Kortenbach et al. |
| 5,632,717 A | 5/1997 | Yoon |
| 5,645,076 A | 7/1997 | Yoon |
| 5,658,236 A | 8/1997 | Sauer et al. |
| 5,658,306 A | 8/1997 | Kieturakis et al. |
| 5,662,613 A | 9/1997 | Astarita |
| 5,662,673 A | 9/1997 | Kieturakis |
| 5,669,885 A | 9/1997 | Smith |
| 5,674,184 A | 10/1997 | Hassler |
| 5,676,156 A | 10/1997 | Yoon |
| 5,676,682 A | 10/1997 | Yoon |
| 5,681,323 A | 10/1997 | Arick |
| 5,685,820 A | 11/1997 | Riek et al. |
| 5,690,663 A | 11/1997 | Stephens |
| 5,690,664 A | 11/1997 | Sauer et al. |
| 5,697,913 A | 12/1997 | Sierocuk et al. |
| 5,707,382 A | 1/1998 | Sierocuk et al. |
| 5,709,671 A | 1/1998 | Stephens et al. |
| 5,716,369 A | 2/1998 | Riza |
| 5,720,761 A | 2/1998 | Kaali |
| 5,738,628 A | 4/1998 | Sierocuk |
| 5,772,660 A | 6/1998 | Young et al. |
| 5,772,678 A | 6/1998 | Thomason et al. |
| 5,776,112 A | 7/1998 | Stephens et al. |
| 5,797,943 A | 8/1998 | Danks et al. |
| 5,797,944 A | 8/1998 | Nobles et al. |
| 5,807,317 A | 9/1998 | Krech, Jr. |
| 5,807,338 A | 9/1998 | Smith et al. |
| 5,817,061 A | 10/1998 | Goodwin et al. |
| 5,827,315 A | 10/1998 | Yoon |
| 5,843,039 A | 12/1998 | Klemm |
| 5,843,115 A | 12/1998 | Morejon |
| 5,857,999 A | 1/1999 | Quick et al. |
| 5,860,996 A | 1/1999 | Urban et al. |
| 5,868,773 A | 2/1999 | Danks et al. |
| 5,873,889 A | 2/1999 | Chin |
| 5,879,332 A | 3/1999 | Schwemberger et al. |
| 5,893,369 A | 4/1999 | LeMole |
| 5,904,699 A | 5/1999 | Schwemberger et al. |
| 5,913,848 A | 6/1999 | Luther et al. |
| 5,916,232 A * | 6/1999 | Hart ............................ 606/185 |
| 5,947,930 A | 9/1999 | Schwemberger et al. |
| 5,971,958 A | 10/1999 | Zhang |
| 5,980,493 A | 11/1999 | Smith et al. |
| 5,980,549 A | 11/1999 | Chin |
| 5,984,941 A | 11/1999 | Wilson et al. |
| RE36,434 E | 12/1999 | Hamlin |
| 5,997,510 A | 12/1999 | Schwemberger |
| 6,007,481 A | 12/1999 | Riek et al. |
| 6,017,356 A | 1/2000 | Frederick et al. |
| 6,022,367 A | 2/2000 | Sherts |
| 6,030,402 A | 2/2000 | Thompson et al. |
| 6,036,657 A | 3/2000 | Milliman et al. |
| 6,039,725 A | 3/2000 | Moenning et al. |
| 6,063,099 A | 5/2000 | Danks et al. |
| 6,099,544 A | 8/2000 | Wolf et al. |
| 6,106,539 A | 8/2000 | Fortier |
| 6,152,871 A | 11/2000 | Foley et al. |
| 6,168,607 B1 | 1/2001 | Wattiez et al. |
| 6,171,281 B1 | 1/2001 | Zhang |
| 6,176,823 B1 | 1/2001 | Foley et al. |
| 6,176,824 B1 | 1/2001 | Davis |
| 6,203,557 B1 | 3/2001 | Chin |
| 6,206,823 B1 | 3/2001 | Kolata et al. |
| 6,209,886 B1 | 4/2001 | Estes et al. |
| 6,228,058 B1 | 5/2001 | Dennis et al. |
| 6,228,059 B1 | 5/2001 | Astarita |
| 6,238,407 B1 | 5/2001 | Wolf et al. |
| D443,360 S | 6/2001 | Haberland |
| 6,245,011 B1 | 6/2001 | Dudda et al. |
| 6,264,604 B1 | 7/2001 | Kieturakis et al. |
| 6,282,442 B1 | 8/2001 | DeStefano et al. |
| D449,887 S | 10/2001 | Haberland et al. |
| 6,319,226 B1 | 11/2001 | Sherry |
| 6,336,914 B1 | 1/2002 | Gillespie, III |
| 6,364,840 B1 | 4/2002 | Crowley |
| 6,478,806 B2 | 11/2002 | McFarlane |
| 6,497,687 B1 | 12/2002 | Blanco |
| 6,497,716 B1 | 12/2002 | Green et al. |
| 6,544,277 B1 | 4/2003 | O'Heeron et al. |
| 6,613,063 B1 | 9/2003 | Hunsberger |
| 6,656,198 B2 | 12/2003 | Tsonton et al. |
| 6,685,630 B2 | 2/2004 | Sauer et al. |
| 6,695,816 B2 | 2/2004 | Cassidy |
| 6,716,201 B2 | 4/2004 | Blanco |

(56) References Cited

U.S. PATENT DOCUMENTS

| | | | |
|---|---|---|---|
| 6,719,746 B2 | 4/2004 | Blanco | |
| 6,719,772 B2 | 4/2004 | Trask et al. | |
| 6,830,578 B2 | 12/2004 | O'Heeron | |
| 6,835,201 B2 | 12/2004 | O'Heeron et al. | |
| 6,837,874 B1 | 1/2005 | Popov | |
| 6,884,253 B1 | 4/2005 | McFarlane | |
| 6,960,164 B2 | 11/2005 | O'Heeron | |
| 6,989,003 B2 | 1/2006 | Wing et al. | |
| D518,177 S | 3/2006 | Blanco | |
| D531,726 S | 11/2006 | Blanco et al. | |
| 7,320,694 B2 | 1/2008 | O'Heeron | |
| 7,344,519 B2 | 3/2008 | Wing et al. | |
| 7,758,603 B2 | 7/2010 | Taylor et al. | |
| 7,824,327 B2 | 11/2010 | Smith | |
| 2001/0029388 A1 | 10/2001 | Kieturakis et al. | |
| 2002/0072713 A1 | 6/2002 | Almond et al. | |
| 2002/0099289 A1 | 7/2002 | Crowley | |
| 2002/0115918 A1 | 8/2002 | Crowley | |
| 2002/0133188 A1 | 9/2002 | O'Heeron et al. | |
| 2002/0143236 A1 | 10/2002 | Sauer et al. | |
| 2002/0188201 A1 | 12/2002 | Crowley | |
| 2003/0100914 A1 | 5/2003 | O'Heeron et al. | |
| 2003/0109894 A1 | 6/2003 | Blanco | |
| 2003/0187471 A1 | 10/2003 | Cooper | |
| 2004/0015182 A1 | 1/2004 | Kieturakis et al. | |
| 2004/0230155 A1 | 11/2004 | Blanco et al. | |
| 2004/0230217 A1 | 11/2004 | O'Heeron | |
| 2005/0038466 A1 | 2/2005 | O'Heeron et al. | |
| 2005/0065543 A1 | 3/2005 | Kahle et al. | |
| 2005/0107816 A1 | 5/2005 | Pingleton et al. | |
| 2005/0119676 A1 | 6/2005 | Bumbalough et al. | |
| 2005/0149096 A1* | 7/2005 | Hilal et al. | 606/191 |
| 2005/0203559 A1 | 9/2005 | O'Heeron | |
| 2005/0209623 A1 | 9/2005 | Patton | |
| 2005/0251190 A1 | 11/2005 | McFarlane | |
| 2005/0261717 A1 | 11/2005 | Sauer et al. | |
| 2006/0030870 A1 | 2/2006 | Staudner | |
| 2006/0149302 A1 | 7/2006 | Popov | |
| 2006/0173479 A1* | 8/2006 | Smith | 606/185 |
| 2006/0200095 A1 | 9/2006 | Steube | |
| 2006/0200182 A1 | 9/2006 | Prosek | |
| 2007/0005087 A1* | 1/2007 | Smith et al. | 606/185 |
| 2007/0010842 A1 | 1/2007 | Popov | |
| 2007/0016237 A1 | 1/2007 | Smith | |
| 2007/0135679 A1 | 6/2007 | Hunt et al. | |
| 2008/0300617 A1* | 12/2008 | Smith | 606/191 |

FOREIGN PATENT DOCUMENTS

| | | |
|---|---|---|
| WO | WO 94-04082 | 3/1994 |
| WO | 03/026512 A1 | 4/2003 |

OTHER PUBLICATIONS

European Search Report for EP 06006907, date of completion Nov. 9, 2006.

Partial European Search Report for EP 06006907, date of completion Aug. 3, 2006.

European Search Report for corresponding EP10252127 date of mailing is Apr. 17, 2012 (8 pgs).

* cited by examiner

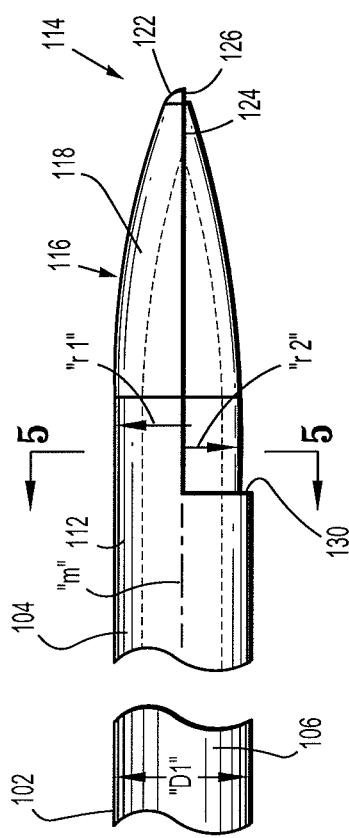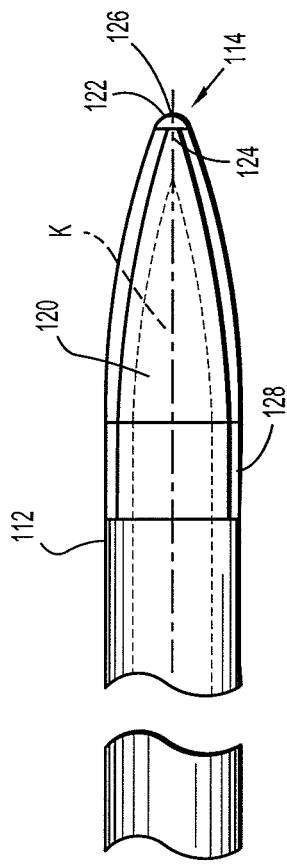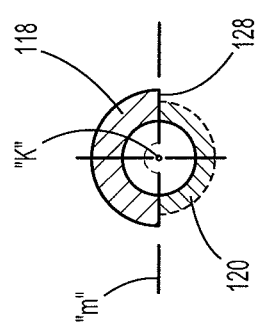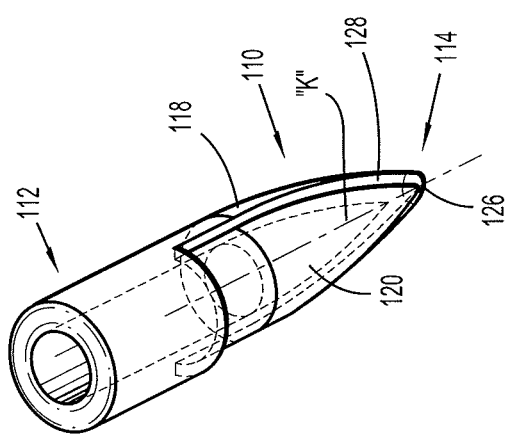

OBTURATOR TIP

CROSS REFERENCE TO RELATED APPLICATION

The present application claims the benefit of and priority to U.S. Provisional Application Ser. No. 61/287,411 filed on Dec. 17, 2009, the entire contents of which are incorporated herein by reference.

BACKGROUND

1. Technical Field

The present disclosure is directed towards an instrument for use in surgical procedures. More particularly, the present disclosure relates to an obturator or dilating member for use with a surgical portal or access assembly.

2. Background of Related Art

Generally, endoscopic and laparoscopic surgical procedures are performed through surgical access devices that include narrow tubular sleeves or cannulas in an insufflated workspace inserted percutaneously into a patient through a small incision, puncture, or access point.

Initially, the incision or access point created in the tissue is very small so as to minimize both tissue trauma and the invasive nature of the procedure. However, to facilitate the insertion of the access device into the patient's tissue, it is often necessary to enlarge or dilate the access point using a surgical instrument such as an obturator, stylet, or trocar. Given the design of known surgical instrument tips, substantial force may be required to insert the instrument through the access point and thereby dilate the opening, potentially resulting in damage or trauma to the tissue surrounding the access point as well as to the internal surgical site. Accordingly, there exists a need in the art for a surgical instrument that includes an improved tip which facilitates the dilation of a percutaneous access point and curtails the risk of tissue damage.

SUMMARY

Accordingly, a surgical instrument for use with a surgical portal apparatus includes an elongate shaft having proximal and distal ends and defining a longitudinal axis and a dilating member disposed at the distal end of the elongate shaft. The dilating member has a first longitudinal arc segment and a second longitudinal arc segment in diametrical opposed relation to the first longitudinal arc segment. The first and second longitudinal arc segments define respective first and second radii of curvature transverse to the longitudinal axis. The first and second radii of curvature decrease from proximal to distal to define a generally tapered configuration of the dilating member. The first radius of curvature is greater than the second radius of curvature at predefined longitudinal positions of the dilating member such that the first longitudinal arc segment extends distally beyond the second longitudinal segment to define a penetrating tip. The penetrating tip has a reduced profile and dimensioned to facilitate initial insertion of the dilating member into tissue.

The first and second radii of curvature may be each dimensioned to decrease in a non-linear manner from distal to proximal or may gradually decrease to define a conic section. The first and second longitudinal arc segments each define a generally semi-hemispherical shape in cross-section.

The penetrating tip may include a substantially planar surface. The elongate shaft may define a radius of curvature greater than a maximum value of the second radius of curvature of the second longitudinal arc segment. The juncture of the second longitudinal arc segment and the elongate shaft defines a vertical surface in general transverse relation to the longitudinal axis. The vertical surface extends about the second longitudinal arc segment. The vertical surface may be substantially planar.

The first longitudinal arc segment and the second longitudinal arc segment may intersect along a median plane of intersection. The first longitudinal arc segment may define a peripheral surface circumscribing an outer periphery of the second longitudinal arc segment. The peripheral surface may be coplanar with the median plane of intersection. The peripheral surface may be substantially planar.

DESCRIPTION OF THE DRAWINGS

The accompanying drawings, which are incorporated in, and constitute a part of this specification, illustrate embodiments of the disclosure and, together with a general description of the disclosure given above and the detailed description of the embodiment(s) given below, serve to explain the principles of the disclosure, wherein:

FIG. 2 is a perspective view of the dilating member of the obturator instrument of FIG. 1;

FIG. 3 is a side plan view of the dilating member of the obturator instrument;

FIG. 4 is a top plan view of the dilating member; and

FIG. 5 is an axial view of the dilating member.

DESCRIPTION OF EMBODIMENTS

Figure 1:
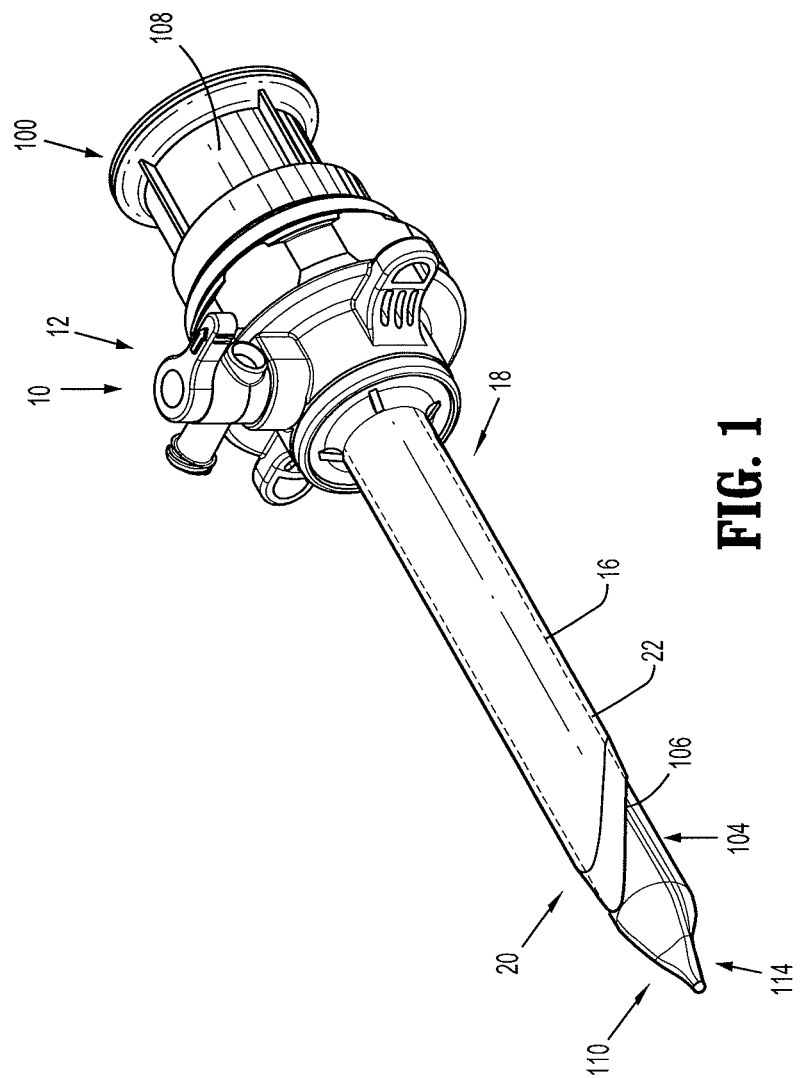
FIG. 1 is a perspective view of a surgical portal system in conjunction with an obturator instrument in accordance with the principles of the present disclosure.

Specific embodiments of the presently disclosed apparatus will now be described in detail with reference to the foregoing figures, wherein like reference numerals identify similar or identical elements. In the figures and in the description which follows, the term "proximal", as is traditional will refer to the end of the apparatus or instrument of the present disclosure which is closest to the clinician, while the term "distal" will refer to the end of the device or instrument which is furthest from the clinician.

Referring now to the drawings, FIG. 1 illustrates a surgical portal or access apparatus 10 and a dilating surgical instrument, member, or obturator 100 in accordance with the present disclosure.

At a proximal end, access apparatus 10 includes a housing 12 configured for the internal receipt of a seal or valve, as is known in the art. Extending distally from housing 12 is a shaft or cannula 16 having respective proximal and distal ends 18, 20 and defining a lumen 22 therethrough. Housing 12, distal end 20 of cannula 16, and the lumen 22 defined therethrough are each dimensioned such that the obturator instrument 100 may pass therethrough.

Referring now to FIGS. 1-3, obturator instrument 100 has a proximal end 102, a distal end 104, and a shaft 106 disposed therebetween. At proximal end 102, obturator instrument 100 is coupled to a gripping member 108 that is configured and dimensioned to facilitate gripping by a clinician, operator, or surgeon. In one embodiment, the gripping member may include a cushioning member or portion that is configured to at least partially absorb the force applied to the gripping member by the clinician, as well as the impact of that force upon the clinician's hand, during the distal advancement of the obturator instrument through a patient's tissue. The cushioning member may be formed of any material that is at least semi-resilient in nature including, but not limited to, polymers. The coupling between proximal end 102 and gripping member 108 may be either fixed or movable, e.g. pivotable, and may be either permanent or releasable.

Shaft 106 of obturator instrument 100 is an elongate member defining a diameter "$D_1$". Diameter "$D_1$" is of a suitable dimension such that shaft 106 does not significantly deform or buckle under the influence of the force applied to the gripping member by the clinician, as discussed above. "$D_1$" may be any diameter substantially within the range of approximately 3 mm to approximately 15 mm. The length of shaft 106 may be of any dimension suitable for the intended purpose of accessing a patient's tissue through the cannula of a surgical access apparatus. Disposed at distal end 104 of obturator instrument 100 is a dilating member or member 110.

Referring now to FIGS. 2-5, in conjunction with FIG. 1, dilating member 110 will be described in detail. Dilating member 110 has a proximal or trailing end 112, a distal or leading end or tip 114, and an outer surface 116 that extends therebetween. Dilating member 110 may be formed of any suitable biocompatible material, including but not limited to polycarbonate, polystyrene, or other suitable polymeric material, and also may be fabricated from stainless steel or the like. Dilating member 110 may be transparent or opaque, and may be either a solid member or at least partially hollow as shown.

Proximal end 112 of dilating member 110 is associated with shaft 106. In one embodiment, shaft 106 and proximal end 112 of dilating member 110 are monolithically formed such that dilating member 110 and shaft 106 are a single unit. In the alternative, dilating member 110 and shaft 106 may be separate components joined to each other during manufacture by any suitable manner including, but not limited to, the use of adhesives, monolithic formation, or welding. In an alternate embodiment, shaft 106 and proximal end 112 of dilating member 110 may be releasably connected through the use of any suitable structural mechanism, including but not limited to, a screw-type or interference-fit arrangement and possibly, joined at the operative site.

Outer surface 116 of dilating member 110 includes a first longitudinal arc segment 118 and a second longitudinal arc segment 120 in diametrical opposed relation to the first longitudinal arc segment 118. Each longitudinal arc segment 118, 120 defines a respective radius of curvature "r1","r2" generally transverse to the longitudinal axis "k". The radii of curvature "r1", "r2" of the first and second longitudinal arc segments 118, 120 generally decrease from proximal end to distal end to define a generally tapered configuration. In one embodiment, the first radius of curvature "r1" of the first longitudinal arc segment 118 is greater than the second radius of curvature "r2" of the second longitudinal arc segment 120 at predefined or common longitudinal positions of the dilating member 110. Accordingly, the first longitudinal arc segment 118 may extend distally beyond the second longitudinal arc segment 120 to define a penetrating or leading tip 114. In one embodiment, the respective radii of curvature "r1", "r2" decrease in a linear manner to define a generally linear taper. In another embodiment depicted in FIGS. 2-5, the respective radii of curvature "r1", "r2" decrease in a non-linear manner providing a non-linear appearance (e.g., parabolic) when viewed in plan. As best depicted in the cross-sectional view of FIG. 5, first and second longitudinal segments 118,120 may define a substantially semi-hemispheric cross-section. In the alternative, the cross-sectional dimensions of each of first and second longitudinal segments 118, 120 may be in the shape of a segment of an ellipse. First and second longitudinal segments 118, 120 may intersect along a median plane of intersection "m" which is coincident with the central longitudinal axis "k", although, in other embodiments, first and second longitudinal segments 118, 120 may intersect along a median plane of intersection "m" which is not coincident with the central longitudinal axis "k."

The maximum value of the first radius of curvature "r1" of the first longitudinal arc segment 118 generally approaches or approximates the radius of curvature of the elongate shaft 106 while the maximum value of the second radius of curvature "r2" of the second longitudinal arc segment 120 is less than that of the elongate shaft 106.

Penetrating tip 114 of dilating member includes leading atraumatic surface 122 of first longitudinal arc segment 118, leading atraumatic surface 124 of second longitudinal arc segment 120 and a substantially planar surface 128 interconnecting the leading atraumatic surfaces 122, 124. Planar surface 128 may or may not extend parallel to the longitudinal axis "k". In one embodiment, planar surface 128 is coincident with the median plane of intersection "m" of first and second longitudinal arc segments 118, 120. The described arrangement presents a substantially reduced profile to penetrating tip 114, which, substantially facilitates initial insertion of the dilating member 110 into tissue. For example, leading atraumatic surface 122 of first longitudinal arc segment 118 may be inserted initially within a path or passage through tissue, or, possibly used to create a path through tissue by virtue of its small axial profile. Leading atraumatic surface 122 may be positioned and advanced within the tissue with relative ease through the presence of the planar surface 126 and the gap extending to the leading atraumatic surface 124 of second longitudinal arc segment 120. Thus, as dilating member 110 is initially advanced, the tissue is dissected along one side of the dilating member 110, i.e., along the first longitudinal arc segment 118. Upon further entry of dilating member 110, second leading surface 124 contacts the tissue to gradually dilate the tissue along the second longitudinal segment 120.

In addition, the arrangement of the respective radii of curvatures "r1", "r2" presents a peripheral surface 128 of first longitudinal arc segment 118 which circumscribes the outer periphery of the second longitudinal segment 120. Peripheral surface 128 may be substantially planar and may be disposed along the median plan of intersection "m" of the first and second longitudinal arc segments 118,120. Peripheral surface 128 provides advantages with respect to approaching the tissue with the dissecting element 110 from an offset or angulated orientation (i.e., without penetrating tip 114 directly engaging the tissue). In this manner, peripheral surface 128 will initially contact the surface. The reduced profile as provided by the planar aspect of peripheral surface 128 facilitates entry within the tissue. A transverse or vertical surface 130 is defined at the juncture of second longitudinal segment 120 and elongate shaft 106 and extends about the second longitudinal arc segment. In one embodiment, vertical surface 130 is dimensioned to provide the clinician with a tactile indicator indicating when the dilating member 110 has passed through the tissue entry location.

Planar surface 126 of penetrating tip 114 and peripheral edge 128 may be substantially blunt or define substantially blunt edges. Planar surface 126 and/or peripheral edge 128 may assist in initially lifting tissue defining a tract away from adjacent tissue portions to facilitate continued insertion of dilating member 110. For example, planar surface 126 and/or peripheral edge 128 may decrease the surface area of the dilating member 110 that is in contact with the patient's tissue (not shown). By decreasing this surface area, any adhesion between the tissue (not shown) and the dilating member 110 that may otherwise occur during the insertion and distal advancement of obturator instrument 100 is substantially minimized.

Although planar surface 126 and peripheral edge 128 of dilating member 110 are depicted as substantially blunt, the inclusion of one or more substantially incisive or sharp edge members, either in addition to or in place of the blunt edge members disclose above, are within the scope of the present disclosure.

Dilating member 110 may include one or more transparent portions such that light is permitted to pass through the dilating member 110. The transparent portions may be formed of any suitable biocompatible material that is at least translucent. Dilating member 110 may include an internal lumen 132 therethrough that is configured and dimensioned to receive an endoscope or other suitable viewing instrument such that a clinician may view a patient's tissue (not shown) via the endoscope and the transparent portions of obturator dilating member 110 during the course of the surgical procedure. Further information regarding the use of optical or transparent materials in surgical access devices may be obtained through reference to commonly assigned U.S. Pat. No. 6,685,630 to Sauer, et al., the entire contents of which are hereby incorporated by reference.

While the above is a complete description of the embodiments of the present disclosure, various alternatives, modifications and equivalents may be used. Therefore, the above description should not be construed as limiting, but rather as illustrative of the principles of the disclosure made herein. Those skilled in the art will envision other modifications within the scope and spirit of the claims appended hereto.

What is claimed is:

1. A surgical instrument for use with a surgical portal apparatus comprising:
   an elongate shaft having proximal and distal ends and defining a longitudinal axis; and
   a monolithic dilating member disposed at the distal end of the elongate shaft, the dilating member having a first longitudinal arc segment and a second longitudinal arc segment in diametrical opposed relation to the first longitudinal arc segment and in secured fixed relation therewith, the first and second longitudinal arc segments defining respective first and second radii of curvature transverse to the longitudinal axis, the first and second radii of curvature decreasing from proximal to distal to define a generally tapered configuration of the dilating member, the first radius of curvature being greater than the second radius of curvature at predefined longitudinal positions of the dilating member such that the first longitudinal arc segment extends distally beyond the second longitudinal segment to define a penetrating tip, the penetrating tip having a reduced profile and dimensioned to facilitate initial insertion of the dilating member into tissue.

2. The surgical instrument of claim 1 wherein the first and second radii of curvature are each dimensioned to decrease in a non-linear manner from distal to proximal.

3. The surgical instrument of claim 2 wherein the first and second longitudinal arc segments each define a generally semi-hemispherical shape in cross-section.

4. The surgical instrument of claim 1 wherein the penetrating tip includes a substantially planar surface.

5. The surgical instrument of claim 1 wherein the elongate shaft defines a radius of curvature greater than a maximum value of the second radius of curvature of the second longitudinal arc segment.

6. The surgical instrument of claim 5 wherein the juncture of the second longitudinal arc segment and the elongate shaft defines a vertical surface in general transverse relation to the longitudinal axis, the vertical surface extending about the second longitudinal arc segment.

7. The surgical instrument of claim 6 wherein the vertical surface is substantially planar.

8. The surgical instrument of claim 1 wherein the first longitudinal arc segment and the second longitudinal arc segment intersect along a median plane of intersection.

9. The surgical instrument of claim 8 wherein the first longitudinal arc segment defines a peripheral surface circumscribing an outer periphery of the second longitudinal arc segment, the peripheral surface coplanar with the median plane of intersection.

10. The surgical instrument of claim 9 wherein the peripheral surface is substantially planar.

11. The surgical instrument of claim 1 wherein the dilating member defines a hollow interior.

12. The surgical instrument of claim 11 wherein the dilating member is at least partially transparent.

13. The surgical instrument of claim 11 wherein the dilating member has a continuous closed outer end.

14. A surgical instrument for use with a surgical portal apparatus comprising:
    an elongate shaft defining a longitudinal axis;
    a dilating member supported at a distal end of the elongate shaft and having a continuous closed outer end, the dilating member having a first longitudinal arc segment and a second longitudinal arc segment being in diametrical relation, the first and second longitudinal arc segments defining first and second radii of curvature transverse to the longitudinal axis, the first radius of curvature being different from the second radius of curvature at predetermined positions along the dilating member, the first and second longitudinal arc segments being secured relative to each other such that the first longitudinal arc segment extends distally beyond the second longitudinal arc segment to define a penetrating tip to facilitate initial insertion of the dilating member into tissue.

15. The surgical instrument of claim 14 wherein the first radius of curvature is greater than the second radius of curvature at predefined positions along the longitudinal axis.

16. The surgical instrument of claim 15 wherein the first longitudinal arc segment and the second longitudinal arc segment intersect along a median plane of intersection.

17. The surgical instrument of claim 16 wherein the first longitudinal arc segment defines a peripheral surface circumscribing an outer periphery of the second longitudinal arc segment, the peripheral surface coplanar with the median plane of intersection.

18. The surgical instrument of claim 17 wherein each of the respective radii of curvature decreases from a proximal end to the penetrating end of the dilating member.

19. The surgical instrument of claim 14 wherein the penetrating tip defines a substantially planar surface.

20. The surgical instrument of claim 14 wherein the dilating member is configured as a substantially solid member.

21. The surgical instrument of claim 14 wherein the dilating member defines a hollow interior.

22. The surgical instrument of claim 21 wherein the dilating member is at least partially transparent.

23. The surgical instrument of claim 14 wherein the dilating member is monolithically formed.

* * * * *